United States Patent [19]

Sharvit et al.

[11] Patent Number: 4,752,644

[45] Date of Patent: Jun. 21, 1988

[54] VAPOR PHASE PRODUCTION OF CHLORINATED PYRIDINES FROM ALPHA-PICOLINE

[75] Inventors: Joseph Sharvit; David Lubetzky; Abraham A. Pereferkovich, all of Beer Sheva, Israel

[73] Assignee: Makhteshim Chemical Works Ltd., Beer-Sheva, Israel

[21] Appl. No.: 32,438

[22] Filed: Mar. 30, 1987

[30] Foreign Application Priority Data

Mar. 31, 1986 [IL] Israel .................................. 78359

[51] Int. Cl.$^4$ ............................................ C07D 213/61
[52] U.S. Cl. .................................................. 546/345
[58] Field of Search ......................................... 546/345

[56] References Cited

U.S. PATENT DOCUMENTS

| | | | |
|---|---|---|---|
| 3,251,848 | 5/1966 | Taplin | 546/345 |
| 3,899,495 | 8/1975 | Beschke et al. | 546/345 |
| 3,960,869 | 6/1976 | Kyi | 546/345 |
| 4,205,175 | 5/1980 | Bowden et al. | 546/345 |
| 4,281,135 | 7/1981 | Perrettie et al. | 546/345 |
| 4,515,953 | 5/1985 | Marinak et al. | 546/345 |
| 4,577,027 | 3/1980 | Marinak et al. | 546/345 |

FOREIGN PATENT DOCUMENTS 1050378 1/1965 United Kingdom .............. 546/345

*Primary Examiner*—Richard A. Schwartz
*Attorney, Agent, or Firm*—Browdy & Neimark

[57] ABSTRACT

2-Chloropyridine, 2,6-dichloropyridine, 2,3,6-trichloropyridine, and 2,3,5,6-tetrachloropyridine are prepared by reacting alpha-picoline in the gas phase with choline at temperature from about 200° C. in the presence of water and an amount of catalyst effective to catalyze the reaction.

26 Claims, No Drawings

VAPOR PHASE PRODUCTION OF CHLORINATED PYRIDINES FROM ALPHA-PICOLINE

BACKGROUND OF THE INVENTION

The present invention concerns the improved process for preparing chlorinated pyridines from alpha-picoline. The present invention particularly concerns the preparation of monochloropyridine, 2,6-dichloropyridine, 2,3,6-trichloropyridine, and 2,3,5,6-tetrachloropyridine.

The chlorinated pyridine derivatives of the present invention are known compounds having been previously prepared by a number of processes. These compounds, namely 2,3,5,6-tetrachloropyridine, have uses such as herbicides, pesticides, etc., and are also employed as chemical intermediates in the preparation of other highly desired herbicide or pesticide products. Previous methods for preparing such compounds include those described in the following patents as well as the prior art noted therein: U.S. Pat. Nos. 3,186,944; 3,370,062; 3,420,833; 3,538,100; 3,732,230; 3,969,205; European Pat. No. 9,212; Great Britain Pat. No. 1,532,038; and Japanese patent publication No. 75/154,266.

Thus, U.S. Pat. No. 3,969,205 describes the photochemical reaction of pyridine and chlorine to prepare 2-chloropyridine. Japanese patent publication No. 75/154,266 describes a similar reaction between chlorine and pyridine or 2-chloropyridine to prepare 2,6-dichloropyridine.

GB No. 1,532,038 describes the preparation of 2,3,5-trichloropyridine by the gas phase reaction of 3,5-dichloropyridine with a large excess of chlorine at temperature of 300°–460° C.

Mixtures of trichloro-, tetrachloro-, and pentachloropyridine are reported by U.S. Pat. No. 3,186,994 to be formed by the chlorination of a polychloro- (trichloromethyl)-pyridine in the liquid phase using either irradiation with ultraviolet light or temperatures above 400° C.

U.S. Pat. No. 3,538,100 describes the preparation of 2,3,5,6-tetrachloropyridine and pentachloropyridine by the chlorination of liquid 2,6-dichloropyridine at a temperature of at least 180° C. in the presence of a metallic halide catalyst.

Picolines have been reported to react with chlorine under a variety of conditions to form mixtures of chloropicolines. Thus, EP No. 9,212 reports using β-picoline in the gas phase in the presence of silica or alumina to form 2-chloro-5-trichloromethylpyridine. U.S. Pat. No. 3,420,833 reports the reaction of α-picoline using carbon tetrachloride or water as a diluent to form a mixture of chlorinated picolines. U.S. Pat. No. 3,732,230 reports the liquid phase chlorination of alpha-picoline hydrochloride containing no more than 5 percent of water. Here too the result was a mixture of chlorinated picolines. In neither of these references listed above involving the chlorination of picoline is there a report of the cleavage of the alkyl group to form chlorinated pyridines. The alkyl group is always preferentially chlorinated; and the resulting trichloromethyl group retained throughout the reaction.

U.S. Pat. No. 3,370,062 reported the reaction of α-picoline with chlorine in the presence of silica or alumina catalysts to primarily form pentachloropyridine. However this process requires the use of a fluidized bed and only affords yields of less than 50 percent. In addition, this reaction proceeded directly to pentachloropyridine, without any ability to obtain the highly desired lower chlorinated pyridines, such as 2,3,5,6-tetrachloropyridine.

OBJECTIVES OF THE INVENTION

It is the objective of the present invention to provide a new and improved method for the production of chloropyridines such as 2-monochloropyridine 2,6-dichloropyridine, 2,3,6-trichloropyridine, and 2,3,5,6-tetrachloropyridine. It is a further objective of the present invention to provide a method more economical than known methods for the production of these compounds substantially free of tarry by-products in yields far in excess of those previously obtained in known methods. A further objective is the provision of a method which affords high yields of the specific chlorinated pyridines depending upon the conditions of the reaction. An additional objective is the provision of a method which gives 2,3,5,6-tetrachloropyridine in high yields.

SUMMARY OF THE INVENTION

It has unexpectedly been discovered that chloropyridines of the formula:

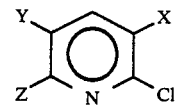

wherein, X, Y, and Z are H or Cl; provided that when X is Cl, Z must be Cl, and further provided that when Y is Cl, Z must be Cl; can be prepared by continuously reacting alpha-picoline with chlorine at a temperature of at least about 200° C. in the gas phase comprising running the reaction in the presence of water and a catalyst selected from the group consisting of silicates and silicate clays and an amount thereof effective to catalyze the said reactions.

The process of the present invention can be conducted to provide mixtures of different chlorinated pyridines, which can be readily separated; or to provide optimum amounts of the desired 2,6-dichloropyridine or 2,3,5,6-tetrachloropyridine, while minimizing the production of pentachloropyridine and other chlorinated pyridine or picoline products. The process of the present invention is preferably carried out to produce the highly preferred 2,3,5,6-tetrachloropyridine. Alternatively the mixtures provided in the present invention may be also used without separation to prepare 2,3,5,6-tetrachloropyridine via a process covered in a copending application.

DETAILED DESCRIPTION OF THE INVENTION

In carrying out the process of the present invention, the alpha-picoline is added as an aqueous solution to an evaporator kept at a temperature of 250° C. The vapors leaving the evaporator are directed into the reactor containing the respective catalysts. An inert gas, such as nitrogen, may be optionally used to assist in the evaporation of the reactants in the evaporator.

The reactor can be made from any material which stands up to the conditions of the present reaction. The reactor can either be a fixed bed or a fluidized bed. Since the reaction is carried out at elevated temperatures, the reactor must be heated to the desired temperature to initiate the reaction. Once the reaction is underway, the exothermic nature of the reaction requires cooling of the reactor to keep the temperature within the described temperature range.

While a lower limit of about 200° C. is required for the present invention, the temperature of the reaction will naturally depend upon the mole ratios of chlorine to alpha-picoline, the type of catalyst, and the desired end-product. As a general rule, temperatures of from about 200° C. to about 500° C. has been found suitable for the reaction of the present invention, with a preferred temperature range of 300° to 450° C.

Chlorine gas is simultaneously passed into the reactor. After passing through the reactor the products and unreacted reactants are collected by cooling and condensation in a collector kept at 0° C. The unreacted chlorine is removed by scrubbing in caustic. Alternatively, it may be optionally separated by known methods and recycled into the reactor. The resulting product is worked up and separated by standard methods to afford high yields of selected lower chlorinated pyridines with essentially no chlorinated picolines.

The reaction of the present invention is run in a continuous manner. The residence time will naturally depend upon the temperature, type of catalyst, and the end-product desired. However, residence times of 1 to 30 seconds and preferably 4–15 seconds are usually employed.

The process of the present invention may be carried out by reacting equimolar amounts of chlorine and alpha-picoline. However, the conversion is not very high, hence, not economically competitive. For economic reasons it is preferred to use an excess of chlorine. Depending upon the desired end-product, a mole ratio of chlorine to alpha-picoline of 1 to 30 has been found suitable. A mole ratio of 2 to 15 is preferred; with a mole ratio of chlorine to alpha-picoline of 3 to 10 most preferred.

Contrary to the prior art listed above, it has been unexpectedly found that the gas phase chlorination of alpha-picoline in the presence of water causes a splitting off of the methyl group bound to the pyridine ring, preferentially forming lower chlorinated pyridines containing up to four chlorine atoms with essentially no chlorinate picolines. The alpha-picoline may be used as a solution in water; with solutions of 1 to 90 percent of alpha-picoline found suitable. However, a concentration of 5 to 50 percent of alpha-picoline in water is preferred. Attempts to run the reaction of the present invention without water or using conventional fillers such as glass beads or carborundum resulted in the overwhelming formation of a mixture of chlorinated picolines.

A catalyst is required in order to obtain the selective formation of chlorinated pyridines from alpha-picoline. Satisfactory catalysts which may be employed are silicates like vemiculite, talc, or pyrophyllite or silicate clays chosen from the attapulgite, montmorillonite, or kaolinite groups. Representative forms of the attapulgite groups are attapulgite or sepiolite. Representative forms of the montmorillonite group are bentonite, saponite, or hectonite. Preferred catalysts are attapulgite, bentonite, and pyrophyllite. The particle size of the catalyst is not particularly critical. Particles of 2–10 mm and preferably 3–6 mm can be used.

While these catalysts are effective when used alone, they are also effective when mixtures of them are used. A representative form of such a mixture is bentonite and pyrophyllite. Weight ratios of bentonite to pyrophyllite of from 1:20 to 20:1 are effective, with weight ratios of bentonite to pyrophyllite of from 1:3 to 1:7 particularly effective.

While the invention will now be described in connection with certain preferred embodiments in the following examples it will be understood that it is not intended to limit the invention to these particular embodiments. On the contrary it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of procedures as well as the principles and conceptual aspects of the invention.

EXAMPLE 1

To an evaporator was pumped in a 50% solution of alpha-picoline in water at a rate of 22 g per hour. Nitrogen gas was swept through the evaporator at a rate of 40 g per hour to aid in the evaporation of the alpha-picoline. The gaseous picoline was fed directly into a tubular glass reactor having a diameter of 35 mm, a length of about 560 mm, and externally electrically heated containing pyrophyllite as catalyst. Simultaneously, chlorine gas was fed into the reactor at a rate of 80 g per hour; and the reaction run for six hours while keeping the reactor at 450° C. by air cooling. The mixture formed was neutralized, extracted with chloroform, the solvent evaporated, and the residue fractinated to afford 12.8 g 2-monochloropyridine, 7.4 g 2,3-dichloropyridine, 41.2 g 2,6-dichloropyridine, and 4.8 g 2,3,6-trichloro-pyridine.

EXAMPLE 2

Following the method of Example 1, but feeding a 5% solution of alpha-picoline in water at a rate of 100 g per hour and 38 g per hour of chlorine gas into the reactor containing attapulgite as catalyst kept at a temperature of 300° C. there was obtained after 12 hours 7.4 g 2,6-dichloropyridine, 2.6 g 2,3-dichloropyridine, 46.6 g 2,3,6-trichloropyridine, and 30.4 g 2,3,5,6-tetrachloropyridine.

EXAMPLE 3

Following the method of Example 1, but feeding a 20% aqueous solution of alpha-picoline at a rate of 36 g per hour and 22 g chlorine gas per hour into the reactor containing bentonite as catalyst kept at a temperature of 300° C. there was obtained after six hours 22 g of 2-chloropyridine and 21.5 g 2,6-dichloropyridine.

EXAMPLE 4

Following the method of Example 1, but feeding a 15% aqueous solution of alpha-picoline at a rate of 90 g per hour and 50 g chlorine gas per hour into the reactor containing a mixture of 85% pyrophyllite and 15% bentonite as catalyst kept at a temperature of 350° C. there was obtained after six and a half hours 43.4 g 2-monochloropyridine and 31.4 g 2,6-dichloropyridine.

EXAMPLE 5

Following the method of Example 3, but adding chlorine at a rate of 17 g per hour, there was obtained 30.7 g 2-chloropyridine and 13.4 g 2,6-dichloropyridine.

EXAMPLE 6

Following the method of Example 1, but running the reaction without any water, there was primarily obtained a mixture of chlorinated picolines.

EXAMPLE 7

Following the method of Example 1, but using glass beads in place of one of the catalysts of the present invention, there was obtained a mixture of chlorinated picolines.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to appended claims, rather than to the foregoing description, and all changes which come with the meaning of equivalency of the claims are therefore intended to be embraced therein.

What is claimed is:

1. A process for preparing chloropyridines of the formula:

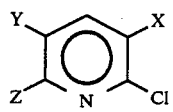

wherein; X, Y, and Z are H or Cl provided that when X is Cl, Z must be Cl; and further provided that when Y is Cl, Z must be Cl;
which comprises continuously reacting alpha-picoline with chlorine in the gas phase at an elevated temperature characterized in that the reaction is conducted in the presence of water and a catalyst selected from the group consisting of silicates and silicate clays and an amount thereof effective to catalyze the reaction.

2. A process in accordance with claim 1 wherein the catalyst is a silicate.

3. A process in accordance with claim 1 wherein the catalyst is pyrophyllite.

4. A process in accordance with claim 1 wherein the catalyst is a silicate clay such as attapulgite, sepiolite, bentonite, saponite, hectonite or kaolinite.

5. A process in accordance with claim 1 wherein the catalyst is attapulgite.

6. A process in accordance with claim 1 wherein the catalyst is bentonite.

7. A process in accordance with claim 1 wherein the catalyst is a mixture of silicates and silicate clays.

8. A process in accordance with claim 1 wherein the catalyst is a mixture of bentonite and pyrophyllite.

9. A process in accordance with claim 8 wherein the mixed catalyst contains bentonite and pyrophyllite in a weight ratio of from 1:20 to 20:1.

10. A process in accordance with claim 9 wherein the bentonite and pyrophyllite are mixed in a weight ratio of from 1:3 to 1:7.

11. A process in accordance with claim 1 wherein the mole ratio of chlorine to alpha-picoline is 1 to 30.

12. A process in accordance with claim 11 wherein the mole ratio of chlorine to alpha-picoline is 2 to 15.

13. A process in accordance with claim 11 wherein the mole ratio of chlorine to alpha-picoline is 3 to 10.

14. A process in accordance with claim 1 wherein the reaction temperature is in the range of from 200° C. to 500° C.

15. A process in accordance with claim 14 wherein the reaction temperature is in the range of from 300° C. to 450° C.

16. A process in accordance with claim 1 wherein the weight ratio of alpha-picoline to water is from 1:99 to 90:1.

17. A process in accordance with claim 16, wherein the weight ratio of alph-picoline to water is from 1:1 to 1:20.

18. A process in accordance with claim 1 wherein the residence time of the mixture in the reaction zone is between 1 to 30 seconds.

19. A process in accordance with claim 18 wherein the residence time of the mixture in the reaction zone is between 4 and 15 seconds.

20. A process for preparing chloropyridines of the formula

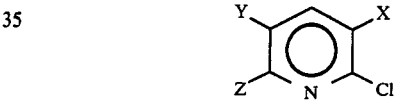

wherein X, Y and Z are H or Cl;
provided that when X is Cl, Z must be Cl; and further provided that when Y is Cl, Z must be Cl;
which comprises continuously reacting chlorine with alpha-picoline in the gas phase in a mole ratio of 3 to 10, respectively, at a temperature between 300° to 450° C. characterized in that the reaction is conducted in the presence of water having a mole ratio of alpha-picoline to water between 1:1 to 1:20 in the presence of a catalyst selected from the group consisting of pyrophyllite, attapulgite, bentonite, and kaolinite.

21. A process in accordance with claim 20 wherein the catalyst is a mixture of bentonite and pyrophyllite.

22. A process in accordance with claim 21 wherein the bentonite and pyrophyllite are present in a weight ratio of from 1:3 to 1:7.

23. A process in accordance with claim 20 wherein the chloropyridine is 2-monochloropyridine.

24. A process in accordance with claim 20 wherein the chloropyridine is 2,6-dichloropyridine.

25. A process in accordance with claim 20 wherein the chloropyridine is 2,3,6-trichloropyridine.

26. A process in accordance with claim 20 wherein the chloropyridine is 2,3,5,6-tetrachloropyridine.

* * * * *

UNITED STATES PATENT AND TRADEMARK OFFICE
CERTIFICATE OF CORRECTION

PATENT NO. : 4,752,644
DATED : June 21, 1988
INVENTOR(S) : SHARVIT et al

It is certified that error appears in the above—identified patent and that said Letters Patent is hereby corrected as shown below: Title page:

IN THE ABSTRACT:

Line 4: change "choline" to read --chlorine--

IN THE SPECIFICATION:
Column 1, line 32: insert --Pat.-- after "GB";
Column 1, lines 34, 35: change the word "temperature" spanning lines 34 and 35 to --temperatures--;

Column 1, line 49: Insert --PAT.-- after "EP";

Column 3, line 46: change "chlorinate" to --chlorinated--;

Column 4, lines 38, 39: change the word "fractinated" spanning lines 38 and 39 to --fractionated--.

Signed and Sealed this

Sixth Day of December, 1988

*Attest:*

DONALD J. QUIGG

*Attesting Officer*      *Commissioner of Patents and Trademarks*